US010032616B2

(12) United States Patent
Zhang et al.

(10) Patent No.: US 10,032,616 B2
(45) Date of Patent: Jul. 24, 2018

(54) SAMPLE INTRODUCTION DEVICE

(71) Applicant: Nuctech Company Limited, Beijing (CN)

(72) Inventors: Qingjun Zhang, Beijing (CN); Yuanjing Li, Beijing (CN); Zhiqiang Chen, Beijing (CN); Weiping Zhu, Beijing (CN); Huishao He, Beijing (CN); Qiufeng Ma, Beijing (CN); Yaohong Liu, Beijing (CN); Xiang Zou, Beijing (CN); Jianping Chang, Beijing (CN)

(73) Assignee: Nuctech Company Limited, Beijing (CN)

( * ) Notice: Subject to any disclaimer, the term of this patent is extended or adjusted under 35 U.S.C. 154(b) by 274 days.

(21) Appl. No.: 14/985,219

(22) Filed: Dec. 30, 2015

(65) Prior Publication Data
US 2016/0189945 A1 Jun. 30, 2016

(30) Foreign Application Priority Data
Dec. 31, 2014 (CN) .......................... 2014 1 0850105

(51) Int. Cl.
*G01N 1/40* (2006.01)
*G01N 1/44* (2006.01)
(Continued)

(52) U.S. Cl.
CPC .......... *H01J 49/0422* (2013.01); *G01N 30/14* (2013.01); *G01N 30/16* (2013.01); *G01N 30/20* (2013.01)

(58) Field of Classification Search
CPC ..... H01J 49/0422; G01N 30/16; G01N 30/14; G01N 30/20; G01N 2030/025;
(Continued)

(56) References Cited

U.S. PATENT DOCUMENTS 4,128,008 A * 12/1978 Linenberg .............. G01N 1/405
73/863.12
6,134,945 A * 10/2000 Gerstel .................. B01D 53/30
422/78
(Continued)

FOREIGN PATENT DOCUMENTS

CN         1296564 A      5/2001
CN       101113968 A      1/2008
(Continued)

OTHER PUBLICATIONS

Office Action received in corresponding German Application No. DE10 2015 226 806.3, dated Jan. 15, 2016, and English language translation thereof; 7 pages total.
(Continued)

*Primary Examiner* — Manish S Shah
*Assistant Examiner* — Anthony W Megna Fuentes
(74) *Attorney, Agent, or Firm* — Knobbe, Martens, Olson & Bear LLP

(57) ABSTRACT

A sample introduction device comprises a sampling unit, a gas suction pump, adsorption units, a piston cylinder and a desorption cylinder that comprises a desorption chamber, a carrier-gas inlet, a split/purge vent and an analyzer nozzle communicating with the desorption chamber. A heating film and a temperature sensor are provided on outer wall of the desorption cylinder. The piston cylinder above the desorption cylinder comprises two piston chambers, each of which is provided with the adsorption unit and in communication with the desorption chamber. The piston cylinder comprises a sample-gas inlet connected to the sampling unit and a gas-suction-pump orifice connected to the gas suction pump, each of which can communicate with both piston chambers. Each adsorption unit comprises an adsorption cylinder-like screen for holding adsorbents and a piston rod slidably mounted in the piston chamber. Each adsorption cylinder- (Continued)

like screen can simultaneously communicate with the sample-gas inlet and gas-suction-pump orifice.

20 Claims, 1 Drawing Sheet

(51) Int. Cl.
    *G01N 30/14*     (2006.01)
    *G01N 30/16*     (2006.01)
    *G01N 30/20*     (2006.01)
    *H01J 49/00*     (2006.01)
    *B01D 53/02*     (2006.01)
    *B01D 59/26*     (2006.01)
    *B01D 15/02*     (2006.01)
    *H01J 49/04*     (2006.01)

(58) Field of Classification Search
    CPC ....... G01N 2030/128; G01N 2030/524; G01N 1/405; B01D 53/025; B01D 53/02; B01D 59/26; B01D 15/02
    USPC ... 73/863.11, 863.12, 863.31, 863.33, 23.35, 73/23.41–23.42; 95/82–89; 96/101–107
    See application file for complete search history.

(56) References Cited

U.S. PATENT DOCUMENTS

| | | | |
|---|---|---|---|
| 6,481,263 | B1 | 11/2002 | Haley et al. |
| 7,449,050 | B2* | 11/2008 | Wohltjen ........... B01D 53/0407 422/88 |
| 7,730,796 | B2* | 6/2010 | Shimada ............. G01N 1/2214 73/863.12 |
| 7,977,113 | B2* | 7/2011 | Donaldson ........... G01N 1/2202 422/401 |
| 9,459,186 | B2* | 10/2016 | Mastromatteo ......... B01L 3/502 |
| 2012/0223226 | A1* | 9/2012 | Rafferty ................ G01N 1/405 250/288 |

FOREIGN PATENT DOCUMENTS

| | | |
|---|---|---|
| CN | 102768262 A | 11/2012 |
| CN | 103245743 A | 8/2013 |
| CN | 103808768 A | 5/2014 |
| CN | 204302250 U | 4/2015 |
| DE | 690 33 217 | 12/1999 |
| DE | 10 2011 002 097 | 2/2012 |
| DE | 11 2010 000 036 | 7/2013 |
| EP | 0447158 | 9/1991 |
| JP | 2002503808 A | 2/2002 |
| WO | WO 99/41601 | 8/1999 |

OTHER PUBLICATIONS

Chinese Office Action dated Nov. 4, 2015 in Chinese Application No. 201410850105.6.

Gan, Jiayi, et al., "Application of Regeneration Technique of Molecular Sieve in Ion Mobility Spectrometer", Science and Technology Information, Issue 11, Apr. 15, 2010, pp. 26 and 38.

Hill, Herbert H. et al., "A Detection Method for Unified Chromatography: Ion Mobility Monitoring" Journal of High Resolution Chromatography, vol. 15, Jul. 31, 1999, pp. 417-423.

Matz, Laura M. et al., "Investigation of Drift Gas Selectivity in High Resolution Ion Mobility Spectrometry with Mass Spectrometry Detection," Jan. 25, 2002, J Am Soc Mass Spectrom, vol. 13: pp. 300-307.

\* cited by examiner

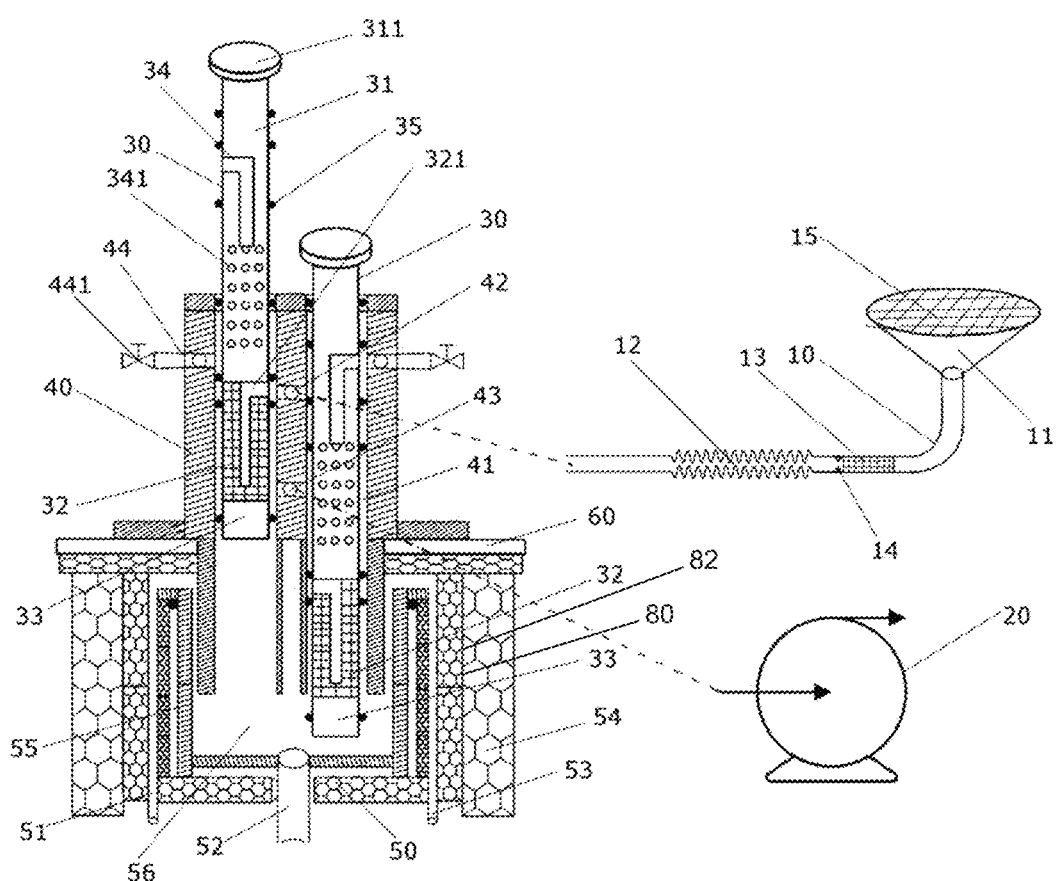

SAMPLE INTRODUCTION DEVICE

CROSS-REFERENCE TO RELATED APPLICATION(S)

This application claims priority to Chinese Patent Application No. 201410850105.6, filed Dec. 31, 2014, published as CN104569228A, and entitled "Sample Introduction Device", which is hereby incorporated by reference in its entirety.

BACKGROUND

Field:

The present invention relates to a field of sample introduction, and more specifically to a sample introduction device.

Description of Related Information:

Ion mobility spectrometer (IMS) is a kind of trace detection device which have recently gained widespread acceptance in the world as she has a very high detect sensitivity, a rapid analyzing speed and a reliable result. The IMS technique identifies samples based mainly on the differences of mobility coefficient of various ions in low electric fields. IMS can rapidly detect drugs, explosives, poisonous gases, biogas and the like, and may be widely employed for military (chemical warfare agent detection) or civil (anti-terrorism, drug control and the like) purposes, and plays an important role in many aspects, such as ensuring national security, maintaining social stability and strengthening national defense and improving national economy and the people's livelihood. However, alarm failures and false alarms are easy to occur when the IMS is solely used to detect complex compounds. Therefore, various combined techniques aimed to improve resolution of analyzer arise. Gas chromatograph-ion mobility spectrometer (GC-IMS) couples GC having an excellent separation capability with IMS having a quick response and a high sensitivity to effectively avoid problems from low identifying capacity of GC and cross sensitivity of IMS when IMS detects mixtures. GC-IMS can obtain three dimensional spectrogram of retention time of color spectrum, drift time and signal intensity, and can effectively identify a sample of complex components. GC-IMS has a detection limit superior to a magnitude of ppb (part per billion) and an identification time ranged from a few minutes to tens of minutes. Compared to other combined techniques, GC-IMS is characterized in simple interfaces, low maintenance cost, high price-quality ratio, etc. Therefore, GC-IMS develops rapidly in recent years, and has advantages of small scale and portability. GC-IMS technique will be one of important tendencies in security check field in the future.

Sample introduction devices are essential to GC-IMS. Sample introduction devices and sample introduction methods have an effect on both a use range of equipment, and a response difficulty and an accuracy of equipment for tested objects. Separate IMS can match with various sample introduction devices, which is a mature technology. Separate GC generally employs headspace sampling methods, which can omit complex pretreatment of samples (suitable for rapid detection). However, with the headspace sampling methods, a certain amount of samples will be "destructively" obtained. Therefore, the headspace sampling methods are not suitable for rapid on-site detection of trace gas without unpacking. Chinese Patent Publication CN1296564A discloses a handheld GC-IMS detector and provides a sampling method for samples attached on surface and gas samples. Specifically, the above reference employs a porous ribbon or coat the ribbon with an absorbing media to adsorb samples of interest, and transmits a portion of the ribbon that has absorbed the samples to a desorption device for sample separation and detection. Although the above reference discloses a rapid detection method adapted for gas samples and samples attached on surface without unpacking, its adsorbing effect is unsatisfactory, and alarm failures and false alarms of instruments are easy to occur.

As such, existing IMS and GC sampling techniques are not suitable for rapid on-site GC-IMS detection without unpacking. Therefore, there is a need for a sample introduction device without unpacking.

OVERVIEW

I. Technical Problem

It is an advantage of aspects of the present innovations to provide a sample introduction device for thermal desorption, which is able to collect volatile or semi-volatile sample molecules or particles of solid sample molecules full time and rapidly, and pre-concentrate the collected samples.

II. Technical Solution

With regard to solution(s) regarding the above, implementations of the present innovations may provide a sample introduction device, comprising: a sampling unit, a gas suction pump, adsorption units, a piston cylinder and a desorption cylinder, the desorption cylinder comprises a desorption chamber, and further comprises a carrier-gas inlet, a split/purge vent and an analyzer nozzle, which are in communication with the desorption chamber; a heating film and a temperature sensor are provided on an outer wall of the desorption cylinder; the piston cylinder comprises two piston chambers, and each piston chamber is provided with a respective adsorption unit; the piston cylinder is mounted above the desorption cylinder, and each of the two piston chambers is in communication with the desorption chamber; the piston cylinder comprises a sample-gas inlet and a gas-suction-pump orifice, each of which is in communication with both of the piston chambers; the sample-gas inlet is connected to the sampling unit, and the gas-suction-pump orifice is connected to the gas suction pump; each adsorption unit comprises an adsorption cylinder-like screen and a piston rod, and the adsorption cylinder-like screen is used for holding adsorbents; each piston rod is slidably mounted in the respective piston chamber and drives the respective adsorption cylinder-like screen to slide along the respective piston chamber and insert into the desorption chamber; and each adsorption cylinder-like screen is able to be simultaneously in communication with the sample-gas inlet and gas-suction-pump orifice.

In one implementation, a thermal insulating layer may be provided on outer wall of the desorption cylinder.

In one implementation, the sample-gas inlet may be connected to the sampling unit via a corrugated pipe, and the sampling unit comprises a bell-like gas suction head having a micro-pore filter.

In one implementation, the adsorption cylinder-like screen may comprise an adsorption screen orifice that is in communication with the sample-gas inlet.

In one implementation, each piston chamber may comprise a respective cooling gas orifice provided with an inlet valve; each piston rod comprises a respective cooling chamber that is able to be in communication with the respective cooling gas orifice; and each piston rod is provided with vents on its side wall, which are in communication with the cooling chamber and are able to be in communication with the gas-suction-pump orifice.

In one implementation, at the bottom of each adsorption cylinder-like screen, a respective heat-insulation pad is provided.

In one implementation, a plurality of sealing rings may be provided between the adsorption unit and the piston chamber.

In one implementation, a liner may be provided on inner wall of the desorption cylinder.

In one implementation, a heat-insulation plate may be provided between the piston cylinder and the desorption cylinder.

In one implementation, the sample-gas inlet may be connected to the sampling unit via a corrugated pipe, in which a drying agent is provided.

III. Advantageous Effects of Invention

In the sample introduction device of the present invention, the sampling unit can directly suction gas sample from surfaces of a tested object or ambient gas atmosphere, and the absorbents in the adsorption cylinder-like screen can perform sample absorption and even sample enrichment. In this way, it is possible to achieve detections without unpacking, reduce sample solution preparation time, and omit devices for headspace work. It is also possible to promote miniaturization and portability of instruments, and facilitate rapid on-site inspections in airports, customs, and the like. In the sample introduction device of the present invention, two adsorption units can be alternatively engaged in testing and can perform a full-time sampling from tested objects. Especially, in case there is a plurality of tested objects, while a previous tested object is analyzed, the sample introduction device can perform sampling and enrichment for a next tested object. This saves overall time of sampling and testing, effectively improves handling capacity and testing speed of analyzer and saves cost. In the sample introduction device of the present invention, by continuous suction of the gas suction pump, samples are pre-concentrated onto the absorbents, and the pre-concentration can reduce the requirement for lower limit of testing of testing devices (such as, IMS, MS [mass spectrometer] and DMS [differential mobility spectrometer]), which reduces developing difficulty and cost of instruments and reduces false alert rate of instruments.

DESCRIPTION OF THE DRAWINGS

FIG. 1 is a schematic view of an embodiment according to the present invention.

REFERENCE SIGNS LIST

10 Sampling Unit
11 Bell-like Gas Suction Head
12 Corrugated Pipe
20 Gas Suction Pump
30 Adsorption Unit
31 Piston Rod
311 Piston Handle
32 Adsorption Cylinder-like Screen
321 Adsorption Screen Orifice
33 Heat-insulation Pad
34 Cooling Chamber
341 Vent
35 Sealing Ring
40 Piston Cylinder
41 Piston Chamber
42 Sample-gas Inlet
43 Gas-suction-pump Orifice
44 Cooling Gas Orifice
441 Inlet Valve
50 Desorption Cylinder
51 Carrier-gas Inlet
52 Analyzer Nozzle
53 Split/Purge Vent
54 Thermal Insulating Layer
55 Liner
56 Desorption Chamber
60 Heat-insulation Plate

DESCRIPTION OF ILLUSTRATIVE IMPLEMENTATIONS

Exemplary implementations will be described in detail with reference to the drawings. However, the present disclosure should not be taken to limit the invention to the specific embodiments shown, but are for explanation and understanding only.

Referring to FIG. 1, an exemplary sample introduction device according to the present inventions may comprise: a sampling unit 10, a gas suction pump 20, adsorption units 30, a piston cylinder 40 and a desorption cylinder 50. The desorption cylinder 50 comprises a desorption chamber 56, an analyzer nozzle 52, a carrier-gas inlet 51 and a split/purge vent 53 which are in communication with the desorption chamber 56. A heating film 80 and a temperature sensor 82 are provided on outer walls of the desorption cylinder 50. The analyzer nozzle is used to connect to a chromatographic column, IMS, MS, or DMS, etc. The carrier-gas inlet is used to connect to a carrier gas supply device to receive carrier gas. The heating film 80 is used to heat the desorption chamber 56. The temperature sensor 82 is used to connect to an external temperature control circuit to read a temperature of the desorption chamber 56 in real time and control the temperature in combination with the external temperature control circuit. Controlling the temperature of the desorption chamber 56 with temperature programmed techniques by a controller can effectively reduce power consumption. The split/purge vent 53 of the desorption cylinder 50 is in communication with the desorption chamber 56. When mixed sample gases shouldn't be totally received through by analyzer from the nozzle 52, a portion of the mixed sample gases will be discharged through the split/purge vent 53. Moreover, the desorption chamber can be purged when the split/purge vent 53 is fully open, and the purging can remove contaminants from the desorption chamber to effectively reduce ghost peaks during sub-sampling. The piston cylinder 40 comprises two piston chambers 41, and each piston chamber 41 is provided with a respective adsorption unit 30. The piston cylinder 40 is mounted above the desorption cylinder 50, and each of the piston chambers 41 is communication with the desorption chamber 56. Lower part of the piston cylinder 40 is inserted into the desorption chamber 56, and there is an opening in the front of the piston chamber 41 and the opening is in communication with the desorption chamber 56. The piston cylinder 40 comprises a sample-gas inlet 42 and a gas-suction-pump orifice 43, each of which is in communication with the both piston chambers 41. The sample-gas inlet 42 is connected to the sampling unit 10 via a corrugated pipe 12, and the gas-suction-pump orifice 43 is connected to the gas suction pump 20. Each adsorption unit 30 comprises an adsorption cylinder-like screen 32 and a piston rod 31 connected to each other. The adsorption cylinder-like screen 32 is a cylinder having pores in its side wall, and is used to hold adsorbent. As a whole, the adsorption unit 30 is shown as a cylindrical piston which is reciprocally movable. The piston rod 31 can be slidably mounted in the piston chamber 41 and drive the adsorption cylinder-like screen 32 to slide along the piston chamber 41 and insert into the desorption chamber 56. The adsorption cylinder-like screen 32 can be simultaneously in communication with the sample-gas inlet 42 and the gas-suction-pump orifice 43. To facilitate push and pull of the piston rod 31, a piston handle 311 is provided at a read end of the piston rod.

In operation, the adsorbent is provided in the adsorption cylinder-like screen 32. The adsorption unit 30 is pulled up at first so that the adsorption cylinder-like screen 32 is in communication with the sampling unit 10 and the gas suction pump 20. The gas suction pump 20 starts suction and then the sampling unit 10 suctions sample gas. Samples in the sample gas are absorbed by the adsorbent when the sample gas flows through the adsorption cylinder-like screen 32. After the sample is accumulated on the adsorbent to an enrichment extent, the adsorption unit 30 is pressed into the preheated desorption chamber 56 for sample desorption. The desorbed sample uniformly mixes with the preheated carrier gas in the desorption chamber 56, which flows into the heat desorption chamber via the carrier-gas inlet 51, and then enters an analyzer such as GC-IMS, IMS, GC-MS, GC-DMS or other types of analyzers via the analyzer nozzle 52 for sample testing. The two adsorption units 30 of the present invention can be used alternatively. That is to say, when one adsorption unit is pulled up for sampling (next sample to be tested), the other is pressed down for sample desorption and testing (previous sample to be tested). In this way, the sample introduction device can rapidly absorb sample in full time, and has significant advantages especially when processing a plurality of samples to be tested. The adsorption unit 30 can concentrate the sample to improve testing accuracy of the analyzer.

Furthermore, the adsorption cylinder-like screen 32 comprises an adsorption screen orifice 321 which is in communication with the sample-gas inlet 42. A sample gas can quickly enter the adsorption cylinder-like screen via the adsorption screen orifice 321. Employing structures like the adsorption screen orifice 321 can effectively increase absorbing area per unit time to increase speed of sample enrichment. Preferably, the sample-gas inlet 42 and the gas-suction-pump orifice 43 are arranged along an axial direction of the piston chamber 41. The distance between the sample-gas inlet 42 and the gas-suction-pump orifice 43 is slightly smaller than the length of the adsorption cylinder-like screen 32 so that the adsorption screen orifice 321 can be appropriately opposed to and in communication with the sample-gas inlet 42. Moreover, a heat-insulation pad 33 at the bottom of the adsorption unit can be unscrewed so that absorbents in the adsorption cylinder-like screen 32 can be replaced. Types of absorbents can be chosen according to testing requirements.

Furthermore, a thermal insulating layer 54 is provided on the outer wall of the desorption cylinder 50. The thermal insulating layer 54 is used to prevent the heat in the desorption chamber 56 of the desorption cylinder 50 from losing too fast to reduce energy consumption. A heat-insulation plate 60 is provided between the piston cylinder 40 and the desorption cylinder 50 to effectively insulate heat transfer between the desorption cylinder 50 and the piston cylinder 40. The heat-insulation plate 60 is screwed to the piston cylinder 40 and the desorption cylinder 50 in a sealing manner. The heat-insulation plate 60 is made of porous ceramic material.

To acquire dry sample gas, a drying agent 13 is provided in the corrugated pipe 12 to absorb moisture from the mixed gases to protect the chromatographic column and the detector. The drying agent 13 is fixed via a slot 14 in the corrugated pipe 12. The sampling unit 10 includes a bell-like gas suction head 11 having a micro-pore filter 15. The micro-pore filter 15 is provided to prevent large-particle substance from entering and blocking the pipes.

Furthermore, each piston chamber 41 comprises a respective cooling gas orifice 44 provided with an inlet valve 441. Each piston rod 31 comprises a respective cooling chamber 34 that is able to be in communication with the respective cooling gas orifice 44. In addition, each piston rod 31 is provided with a plurality of vents 341 in communication with the respective cooling chamber 34 on side wall of the piston rod 31, and at least a part of the vents 341 are able to be in communication with the gas-suction-pump orifice. When the adsorption unit 30 is needed to be cooled, the adsorption unit 30 is pulled up so that the cooling chamber 34 is in communication with the cooling gas orifice 44. The inlet valve 441 is opened, and cooling gas enters via the cooling gas orifice 44 by means of the gas suction pump to cool the piston rod 31 and the adsorption cylinder-like screen 32.

Furthermore, a plurality of O-type sealing rings 35 is provided between the adsorption unit 30 and the piston chamber 41 to play a role of sealing. Moreover, sealing rings 35 can insulate the cooling chamber 34 from the adsorption cylinder-like screen 32 to prevent cooling gas from entering the adsorption cylinder-like screen 32.

Furthermore, a liner 55 is provided on the inner wall of the desorption cylinder 50. The desorption cylinder 50 can be made of stainless steel. The liner 55 is hermetically inserted into the desorption cylinder 50, and is made of Polytetrafluoroethylene (PTFE) material which is chemically stable. The liner 55 can be replaced at regular intervals. On one side, it can be ensured that sample gas does not contact to and react with metal material which will result in distortion of tested sample and signal for testing. On the other side, large-particle substance can be prevented from falling into and blocking the chromatographic column.

Preferably, at the bottom of each adsorption cylinder-like screen 32, a heat-insulation pad 33 is provided to insulate heat in the desorption chamber 56 to prevent heat in the desorption chamber 56 from transferring to the adsorption cylinder-like screen 32. Preferably, the adsorption cylinder-like screen 32 is open at its bottom, and the heat-insulation pad 33 is screwed to the adsorption cylinder-like screen 32. Absorbents can be replaced by pulling out the adsorption unit 30 or unscrewing the piston cylinder 40 and then unscrewing the heat-insulation pad at the bottom of the adsorption unit 30. Users can choose an appropriate type of absorbents (diameter of filled absorbents should be larger than diameter of pores of the adsorption cylinder-like screen 32) according to different testing purposes to improve flexibility of instruments. The heat-insulation pad can be made of PTFE with good heat-insulation property. The heat-insulation pad can effectively ensure that temperatures of the adsorption cylinder-like screen 32 and the absorbents close to ambient temperature during sample enrichment in the sampling unit 30 so as to benefit adsorption and enrichment of sample.

Preferably, the piston rod 31 and the adsorption cylinder-like screen 32 of the sampling unit 30 are integrally manufactured, and are made of heat resistant material that is chemically stable, such as PTFE. The piston cylinder 40 can be made of PTFE material with a high strength, a good heat resistance and stable chemical properties. In order to make the adsorption unit 30 movable stably along the piston chamber 41, guide rails are hermetically arranged in the piston chamber 41 to provide support and sealing pipes for sampling, enriching, air cooling and thermal desorption.

Referring to FIG. 1, for convenience of description, among the two adsorption units, the adsorption unit on left of FIG. 1 is denoted as a first adsorption unit, and the adsorption unit on right of FIG. 1 is denoted as a second adsorption unit. When a sampling process is performed for an object to be tested, the heating film on outer wall of the desorption cylinder is turned on at first and an appropriate temperature is set. After the temperature is stabilized, the two adsorption units are pressed into the desorption chamber such that the absorbents can be purified. Then, the two adsorption units are pulled up, wherein the first adsorption unit is pulled up to the position in which the left adsorption unit is located in FIG. 1, and the second adsorption unit is pulled up to the position in which upper part of the adsorption cylinder-like screen is slightly lower than the sample-gas inlet on upper part of the piston cylinder (no extraction circuit is formed, which facilitates cooling of the adsorption units and subsequent absorption of sample). The gas suction pump for sampling is powered on, and the bell-like sampling head of the sampling unit is oriented towards the object to be tested in close distance. Volatile gas from the object to be tested is collected with the gas suction pump for 3-5 minutes to achieve sample enrichment. After sample enrichment, the adsorption cylinder-like screen of the first adsorption unit is entirely pressed into the desorption chamber for sample desorption. At the same time, the second adsorption unit is pulled up to the position in which the sample-gas inlet, the adsorption cylinder-like screen and the gas-suction-pump orifice form a gas circuit. The above steps are repeated to achieve a rapid and full-time sampling and enrichment separation of various tested objects. The desorbed sample to be tested homogeneously and rapidly mixes with the carrier gas entering via the carrier gas inlet, and then enters a sample outlet. In this way, a desorption sampling is achieved. The sample outlet is connected to a testing device or a separation device.

The advantages of the present invention will be summarized as follows.

I. The sample introduction device of the present invention can directly suction gas sample from surfaces of a tested object or ambient gas atmosphere without unpacking, which reduces space and solution preparation time, promotes miniaturization and portability of instruments, facilitates rapid on-site inspections in airports, customs, and the like.

II. The sample introduction device of the present invention can perform a full-time sampling from tested objects. Especially, in case there is a plurality of tested objects, while a previous tested object is analyzed, the sample introduction device can perform sampling and enrichment for a next tested object. This saves overall time of sampling and testing, effectively improves handling capacity and testing speed of analyzer and saves cost.

III. The sample introduction device of the present invention can pre-concentrate samples. By continuous suction of the gas suction pump, samples are pre-concentrated onto absorbent, and the pre-concentration can reduce the requirement of combined instruments for lower limit of testing of IMS, which reduces developing difficulty and cost of instruments and reduces false alert rate of instruments.

While the invention has been described with reference to exemplary embodiments thereof, it is to be understood that the invention is not limited to the disclosed embodiments or constructions. It should be understood by those skilled in the art that various modifications, combinations, sub-combinations and alterations may occur within the spirit and scope of the invention insofar as they are within the scope of the appended claims or the equivalents thereof.

What is claimed is:

1. A sample introduction device, comprising:
   a sampling unit,
   a gas suction pump,
   one or more adsorption units,
   a piston cylinder, and
   a desorption cylinder, comprising
   a desorption chamber,
   a carrier-gas inlet, a split/purge vent and an analyzer nozzle, which are in communication with the desorption chamber, and
   a heating film and a temperature sensor provided on an outer wall of the desorption cylinder;
   wherein the piston cylinder comprises two piston chambers, and each piston chamber is provided with a respective adsorption unit;
   wherein the piston cylinder is mounted above the desorption cylinder, and each of the two piston chambers is in communication with the desorption chamber;
   wherein the piston cylinder comprises a sample-gas inlet and a gas-suction-pump orifice, each of which is in communication with both of the piston chambers;
   wherein the sample-gas inlet is connected to the sampling unit, and the gas-suction-pump orifice is connected to the gas suction pump;
   wherein each adsorption unit comprises an adsorption cylinder screen and a piston rod, and the adsorption cylinder screen is used for holding adsorbents;
   wherein each piston rod is slidably mounted in the respective piston chamber and drives the respective adsorption cylinder screen to slide along the respective piston chamber and insert into the desorption chamber; and
   wherein each adsorption cylinder screen is able to be simultaneously in communication with the sample-gas inlet and gas-suction-pump orifice.

2. The sample introduction device according to claim 1, wherein a thermal insulating layer is provided on the outer wall of the desorption cylinder.

3. The sample introduction device according to claim 1, wherein the sample-gas inlet is connected to the sampling unit via a corrugated pipe, and the sampling unit comprises a gas suction head having a micro-pore filter.

4. The sample introduction device according to claim 1, wherein the adsorption cylinder screen comprises an adsorption screen orifice that is in communication with the sample-gas inlet.

5. The sample introduction device according to claim 1, wherein each piston chamber comprises a respective cooling gas orifice provided with an inlet valve; each piston rod comprises a respective cooling chamber that is able to be in communication with the respective cooling gas orifice; and each piston rod is provided with vents on its side wall, which are in communication with the cooling chamber and are able to be in communication with the gas-suction-pump orifice.

6. The sample introduction device according to claim 1, further comprising a heat insulation pad provided at a bottom of each adsorption cylinder screen.

7. The sample introduction device according to claim 1, further comprising a plurality of sealing rings provided between each adsorption unit and its respective piston chamber.

8. The sample introduction device according to claim 1, further comprising a liner is provided on an inner wall of the desorption cylinder.

9. The sample introduction device according to claim 1, further comprising a heat-insulation plate is provided between the piston cylinder and the desorption cylinder.

10. The sample introduction device according to claim 1, wherein the sample-gas inlet is connected to the sampling unit via a corrugated pipe, in which a drying agent is provided.

11. The sample introduction device according to claim 2, wherein the sample-gas inlet is connected to the sampling unit via a corrugated pipe, and the sampling unit comprises a gas suction head having a micro-pore filter.

12. The sample introduction device according to claim 2, wherein the adsorption cylinder screen comprises an adsorption screen orifice that is in communication with the sample-gas inlet.

13. The sample introduction device according to claim 2, wherein each piston chamber comprises a respective cooling gas orifice provided with an inlet valve; each piston rod comprises a respective cooling chamber that is able to be in communication with the respective cooling gas orifice; and each piston rod is provided with vents on its side wall, which are in communication with the cooling chamber and are able to be in communication with the gas-suction-pump orifice.

14. The sample introduction device according to claim 2, further comprising a heat insulation pad provided at a bottom of each adsorption cylinder screen.

15. The sample introduction device according to claim 2, further comprising a plurality of sealing rings provided between each adsorption unit and its respective piston chamber.

16. The sample introduction device according to claim 2, further comprising a liner provided on an inner wall of the desorption cylinder.

17. The sample introduction device according to claim 2, further comprising a heat-insulation plate provided between the piston cylinder and the desorption cylinder.

18. The sample introduction device according to claim 2, wherein the sample-gas inlet is connected to the sampling unit via a corrugated pipe, in which a drying agent is provided.

19. The sample introduction device according to claim 18, wherein the sampling unit comprises a gas suction head having a micro-pore filter.

20. The sample introduction device according to claim 19, wherein each piston chamber comprises a respective cooling gas orifice provided with an inlet valve; each piston rod comprises a respective cooling chamber that is able to be in communication with the respective cooling gas orifice; and each piston rod is provided with vents on its side wall, which are in communication with the cooling chamber and are able to be in communication with the gas-suction-pump orifice.

\* \* \* \* \*